United States Patent
Bernadino et al.

(10) Patent No.: US 6,900,344 B2
(45) Date of Patent: May 31, 2005

(54) METHOD OF PREPARING ALKYLATED SALICYLAMIDES VIA A DICARBOXYLATE INTERMEDIATE

(75) Inventors: Joseph N. Bernadino, Stamford, CT (US); Doris C. O'Toole, Carmel, NY (US); William E. Bay, Ridgefield, CT (US)

(73) Assignee: Emisphere Technologies, Inc., Tarrytown, NY (US)

( * ) Notice: Subject to any disclaimer, the term of this patent is extended or adjusted under 35 U.S.C. 154(b) by 0 days.

(21) Appl. No.: 10/239,477

(22) PCT Filed: Mar. 21, 2001

(86) PCT No.: PCT/US01/09154

§ 371 (c)(1),
(2), (4) Date: Sep. 20, 2002

(87) PCT Pub. No.: WO01/70219

PCT Pub. Date: Sep. 27, 2001

(65) Prior Publication Data

US 2003/0096992 A1 May 22, 2003

Related U.S. Application Data

(60) Provisional application No. 60/191,284, filed on Mar. 21, 2000, and provisional application No. 60/191,285, filed on Mar. 21, 2000.

(51) Int. Cl.[7] .................. C07C 229/00; C07C 233/00; C07C 235/00; C07C 237/00; C07C 239/00
(52) U.S. Cl. ..................... 560/38; 560/39; 562/444; 562/450; 564/177; 564/179
(58) Field of Search ................. 562/444, 450; 560/38, 39; 564/177, 179

(56) References Cited

U.S. PATENT DOCUMENTS

| | | | |
|---|---|---|---|
| 2,835,668 A | 5/1958 | Shapiro et al. | 260/244 |
| 4,795,832 A | 1/1989 | Leinen et al. | 564/134 |
| 5,442,092 A | 8/1995 | Chopdekar et al. | 560/65 |
| 5,773,647 A | 6/1998 | Leone-Bay et al. | 562/444 |
| 6,399,798 B2 | 6/2002 | Gschneidner et al. | 554/35 |

FOREIGN PATENT DOCUMENTS

| | | | |
|---|---|---|---|
| GB | 1069367 | 5/1967 | |
| WO | 9710197 | 3/1997 | C07C/51/14 |
| WO | 0040539 | 7/2000 | C07C/59/88 |
| WO | 0046182 | 8/2000 | C07C/229/14 |

OTHER PUBLICATIONS

Shibuya et al, "Synthesis of the Naphthalenedicarboxylic Acid Derivative Obtained From Neocarzinostatin (NCS): A Structure Revision" Tetrahedron Letters, vol. 25(11), pp. 1171–1174 (1984).*
Mazzotta et al, "Esteri ed Ammidi di Saliciloilamminoacidi" Il Farmaco—Ed. Sc. vol. 30(5), pp. 399–407 (1975).*
Steffan et al, "N–Salicyloylaspartic Acid: A New Phenolic Compound in Grapevines" Vitis, vol. 27(2), pp. 79–86 (1988).*
The Gabriel Synthesis of Primary Amines, M.S. Gibson and R.W. Bradshaw, *Agnew. Chem. Internet. Edit. vol. 7 (1968) No. 12.,* p.p. 919–930.
Synthesis, stabilityand anticonvulsant activity of two new GABA prodrugs; F. Palagiano, et al,; *Pharmazie 52 (1997) vol. 4.* pp. 272–276.
O,O–Diethyldithiophoric acid–A new condensing agent for acylation of amines bycarboxylic acid, Md N. Hossain & N Borthakur, *Indian Journal of Chemistry, vol. 28B, Nov. 1990* pp. 1062–1063.
Nitrile sulphides, Part 7. Synthesis of [1]Benzopyrano[4, 3–c]isothiazoles and Isothiazolo[4,3–c]quinolines, Peter A. Brownsort and R. Michael Paton, *J. Chem. Soc. Perkin Trans. I 1987.* pp 2339–2344.
International Search Report mailed Jun. 22, 2001 for International Application No. PCT/US01/09154.

* cited by examiner

Primary Examiner—Mukund J. Shah
Assistant Examiner—Zachary C. Tucker
(74) Attorney, Agent, or Firm—Darby & Darby

(57) ABSTRACT

The present invention relates to a method of preparing an alkylated salicylamide from a protected and activated salicylamide via a dicarboxylated salicylamide intermediate. The present invention also relates to dicarboxylic salicylamide delivery agent compounds for the delivery of active agents. Methods of administration are provided as well.

32 Claims, No Drawings

METHOD OF PREPARING ALKYLATED SALICYLAMIDES VIA A DICARBOXYLATE INTERMEDIATE

This application is a U.S. national phase application under 35 U.S.C. §371 of International Application No. PCT/US01/09154 filed Mar. 21, 2001, which claims the benefit of U.S. Ser. Nos. 60/191,284 and 60/191,285, both of which were filed on Mar. 21, 2000. The entire disclosures of the prior applications are incorporated herein by reference. The international application was published in the English language on Sep. 27, 2001 under Publication No. WO 01/70219.

FIELD OF THE INVENTION

The present invention relates to a method of preparing alkylated salicylamides from salicylamides via a dicarboxylate intermediate. The alkylated salicylamides prepared by this method are suitable for use in compositions for delivering active agents via oral or other routes of administration to animals. Furthermore, the present invention relates to dicarboxylic salicylamides and their salts for delivering active agents, such as biologically or chemically active agents, to a target.

BACKGROUND OF THE INVENTION

Carsalam (2H-1,3-benzoxazine-2,4(3H)-dione) is known in the art as an analgesic (see Merck Index, 12$^{th}$ edition, #1915).

Alkylated salicylamides, such as those disclosed in U.S. Pat. Nos. 5,650,386, 5,773,647, and 5,866,536, have been found to be highly effective as delivery agents for active agents, particularly for oral administration of active agents. Typically, these alkylated salicylamides are prepared by modifying an amino acid or an ester thereof. For example, these alkylated salicylamides may be prepared by acylation of an amino acid or an ester thereof with agents having a leaving group, such as a halogen, carbonyl group, or sulfonyl group, and an appropriate radical to yield the desired modification in the final product. See, for example, U.S. Pat. No. 5,650,386.

International Publication No. WO 00/46182 discloses a method for preparing an alkylated salicylamide by alkylating a protected/activated salicylamide and deprotecting and deactivating the protected/activated salicylamide. The alkylating agent may be, for example, ethyl 10-bromo-decanoate and ethyl 8-bromo-octanoate.

Alternate methods of producing alkylated salicylamides would be useful, especially where raw materials are expensive, yields are low, and reaction conditions are difficult.

Therefore, there is a need for simpler and less expensive methods of preparing alkylated salicylamides.

SUMMARY OF THE INVENTION

The present invention relates to a method of preparing an alkylated salicylamide from a protected and activated salicylamide (hereinafter referred to as a "protected/activated salicylamide") via a dicarboxylated salicylamide intermediate.

The present invention includes a dicarboxylated salicylamide intermediate having the formula

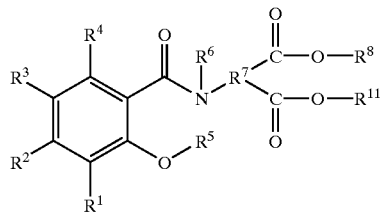

where $R^1$, $R^2$, $R^3$, and $R^4$ are independently hydrogen; halogen; $C_1$–$C_4$ alkoxy, optionally substituted with —OH or F; —OH; $C_1$–$C_4$ alkyl, optionally substituted with —OH or F; —COOH; —OC(O)CH$_3$; —SO$_3$H; nitrile; or —NR$^9$R$^{10}$;

$R^5$ is a protecting group;

$R^6$ is an activating group; or $R^5$ and $R^6$ are combined to form a substituted or unsubstituted cyclic group, i.e., $R^5$ and $R^6$ form a single group that forms a heterocycle with the oxygen atom and nitrogen atom of the amide moiety;

$R^7$ is a linear or branched, $C_1$–$C_{20}$ alkylene, alkenylene, or alkynylene;

$R^7$ is optionally substituted with $C_1$–$C_4$ alkyl, $C_1$–$C_4$ alkenyl, oxygen, nitrogen, sulfur, halogen, —OH, $C_1$–$C_4$ alkoxy, aryl, heteraryl, or vinyl;

$R^7$ is optionally interrupted with aryl, heteroaryl, vinyl, oxygen, nitrogen, or sulfur;

$R^8$ and $R^{11}$ are independently $C_1$–$C_4$ alkyl or $C_1$–$C_4$ haloalkyl; and $R^9$ and $R^{10}$ are independently hydrogen, $C_1$–$C_4$ alkyl, or oxygen.

The dicarboxylated salicylamide intermediate may be prepared by alkylating a protected/activated salicylamide with a dicarboxylate alkylating agent. In one embodiment, the alkylated salicylamide is prepared by (a) deprotecting and deactivating the salicylamide, and (b) optionally, hydrolyzing the deprotected and deactivated salicylamide. In another embodiment, the alkylated salicylamide is prepared by (a) deprotecting and deactivating the salicylamide, (b) optionally, hydrolyzing the deprotected and deactivated salicylamide; and (c) decarboxylating the salicylamide. Steps (a) and (b) may be performed before or after step (c). Preferably, step (c) is performed after steps (a) and (b). According to one embodiment, the deactivating and hydrolysis steps occur simultaneously and after deprotection. The alkylated salicylamides prepared by this method are suitable for use in compositions for delivering active agents via oral or other routes of administration to animals.

Many of the alkylating agents disclosed in the prior art such as ethyl 10-bromo-decanoate and ethyl 8-bromo-octanoate as disclosed in International Publication No. WO 00/46182, are prepared from the dicarboxylate alkylating agents of the present invention. The process for converting the dicarboxylate compounds to the alkylating agents of the prior art is often expensive and time consuming. For example, ethyl 8-bromo-octanoate is prepared from 2-(6-bromohexyl)malonic acid diethyl ester by a multi-step process which includes an expensive distillation step. The process of the present invention reduces the number of synthetic steps required to prepare alkylated salicylamides and, therefore, reduces their manufacturing cost and time.

The present inventors have also discovered that dicarboxylic compounds having the formula

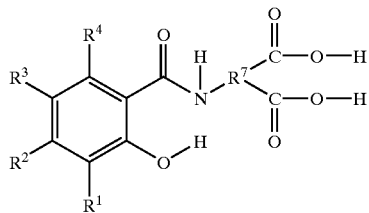

and salts thereof, wherein $R^1$, $R^2$, $R^3$, $R^4$, and $R^7$ are defined as above, facilitate the delivery of active agents. According to a preferred embodiment, $R^7$ is —$(CH_2)_n$—, where n is 4 to 10 and more preferably 7 to 9. According to a preferred embodiment, $R^1$, $R^2$, $R^3$, and $R^4$ are independently hydrogen, halogen, or $C_1$–$C_4$ alkoxy. According to a preferred embodiment, $R^1$, $R^2$, $R^3$, and $R^4$ are independently hydrogen, chlorine, or methoxy. Preferred combinations of $R^1$, $R^2$, $R^3$, and $R^4$ are (H, H, H, H); (H, —$OCH_3$, H, H); and (H, H, Cl, H). The terms "delivery agents" and "delivery agent compounds" as used herein refer to the dicarboxylic compounds of the present invention and alkylated salicylamides prepared by the method of the present invention.

One embodiment is a composition comprising at least one of the delivery agent compounds and at least one active agent. These compositions deliver active agents to biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal in need of the active agent, by administering a composition comprising at one of the delivery agent compounds and the active agent to the animal. Preferred routes of administration include the oral, intracolonic and pulmonary routes.

Yet another embodiment is a method of treating a disease or for achieving a desired physiological effect in an animal by administering the composition of the present invention.

Yet another embodiment is a method of preparing a composition of the present invention by mixing at least one delivery agent compound and at least one active agent.

DETAILED DESCRIPTION OF THE INVENTION

The terms "alkyl", "alkenyl", and "alkynyl" as used herein include linear and branched alkyl, alkenyl, and alkynyl substituents, respectively.

The term "substituted" as used herein refers to compounds substituted with one or more of $C_1$–$C_4$ alkyl, $C_2$–$C_4$ alkenyl, and $C_2$–$C_4$ alkynyl.

The term "protected salicylamide" is defined herein as a salicylamide where the hydroxy moiety of the salicyl group has been protected to prevent reaction of the hydroxy moiety. The term "activated salicylamide" is defined herein as a salicylamide where the nitrogen atom of the amide group has been activated so that the nitrogen atom is in a more reactive condition, i.e., more prone to reaction.

Any of the protected/activated salicylamides in International Publication No. WO 00/46182, which is hereby incorporated by reference, may be used in the process of the present invention. Suitable protected/activated salicylamides include, but are not limited to, compounds having the formula

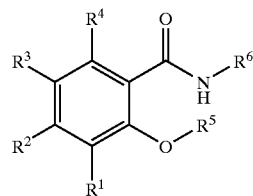

where $R^1$, $R^2$, $R^3$, and $R^4$ are independently hydrogen; halogen; $C_1$–$C_4$ alkoxy, optionally substituted with —OH or F; —OH; $C_1$–$C_4$ alkyl, optionally substituted with —OH or F; —COOH; —OC(O)$CH_3$; —$SO_3$H; nitrile; or —$NR^9R^{10}$;

$R^9$ and $R^{10}$ are independently hydrogen, $C_1$–$C_4$ alkyl, or oxygen;

$R^5$ is a protecting group;

$R^6$ is an activating group; or $R^5$ and $R^6$ are combined to form a substituted or unsubstituted cyclic group, i.e., $R^5$ and $R^6$ form a single group that forms a heterocycle with the oxygen atom and nitrogen atom of the amide moiety.

Preferred halogens for $R^1$, $R^2$, $R^3$, and $R^4$ are chlorine, bromine, and fluorine. Preferred alkoxy groups for $R^1$, $R^2$, $R^3$, and $R^4$ include, but are not limited to, methoxy and ethoxy.

The protecting and activating groups may be the same or different. The protecting and activating groups may be separate moieties (each attached to one of the hydroxy or amide moieties) or a single moiety (attached to both the hydroxy and amide moieties).

Suitable protecting groups include, but are not limited to, —C(O)$CH_3$; —C(O)$F_3$; —S(O)$_2CH_3$; —S(O)$_2CF_3$; benzyl; silyl; tetrahydropyranyl; and methylenealkoxy, such as methylenemethoxy and methyleneethoxy. Suitable activating groups include, but are not limited to, —C(O)$CH_3$; —C(O)$CF_3$; —S(O)$_2CH_3$; and —S(O)$_2CF_3$. Preferably, $R^5$ and $R^6$ are combined to form a cyclic group which protects the hydroxy moiety and activates the nitrogen atom of the amide moiety. More preferably, combined $R^5$ and $R^6$ are —C(O)— or —S(O)$_2$—.

Preferred protected/activated salicylamides include, but are not limited to, carsalam and derivatives thereof having the formula

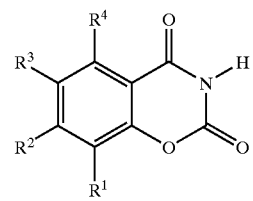

where $R^1$, $R^2$, $R^3$, and $R^4$ are defined as above. One preferred carsalam derivative has the formula above, where $R^1$, $R^2$, $R^3$, and $R^4$ are independently hydrogen, $C_1$–$C_4$ alkoxy, or halogen. Another preferred carsalam derivative has the formula above, where $R^1$, $R^2$, $R^3$, and $R^4$ are independently hydrogen, methoxy, or chlorine. Yet another preferred carsalam derivative has the formula above, where $R^1$, $R^3$, and $R^4$ are hydrogen and $R^2$ is methoxy. Yet another preferred carsalam derivative has the formula above, where $R^1$, $R^2$, and $R^4$ are hydrogen and $R^3$ is chlorine.

Carsalam has the formula

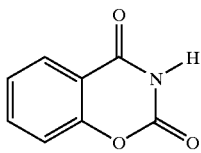

Carsalam may be prepared by methods known in the art, such as those described in Shapiro et al., *JACS*, 79:2811 (1957), and D. N. Dhar, A. K. Bag, *Indian J. Chem.*, 21B:266 (1982). The aforementioned carsalam derivatives may be prepared by methods known for preparing carsalam substituting appropriate starting materials. These carsalam derivatives may also be prepared by adding the appropriate substituents to carsalam by methods known in the art.

One method of preparing the protected/activated salicylamide of the present invention comprises protecting the hydroxy moiety of a salicylamide and activating the amide moiety of the salicylamide, such as that described in International Publication No. WO 00/46182. The protecting and activating steps may be performed in any order, but are preferably performed simultaneously. Alternatively, the protecting step may be performed before performing the activating step.

Suitable (unprotected and unactivated) salicylamides include, but are not limited to, those having the formula

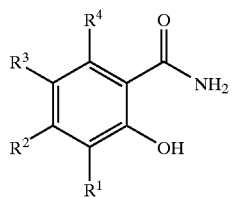

where $R^1$, $R^2$, $R^3$, and $R^4$ are defined as above. Representative unprotected and unactivated salicylamides include, but are not limited to, salicylamide, 4-methoxy salicylamide, and 5-chloro salicylamide.

The hydroxy moiety of the salicylamide may be protected by methods known in the art. For example, the hydroxy moiety may be protected by reacting the salicylamide with a protecting agent, such as an activated halide. The resulting salicylamide has a protecting group attached to the oxygen atom of the hydroxy moiety. Examples of activated halides include, but are not limited to, acyl halides; silyl halides, such as silyl chlorides; benzyl halides; and methylene alkoxy halides, such as methylene methoxy halides and methylene ethoxy halides. Preferably, the reaction with an activated halide is performed in the presence of a base, such as potassium carbonate, triethylamine, or pyridine.

Another example of a protecting agent is an activated ether. Examples of activated ethers include, but are not limited to, dihydropyranyl ether. Preferably, the activated ether is reacted with the salicylamide under acid catalysis conditions, such as with sulfuric acid, para-toluene sulfonic acid, or camphor sulfonic acid in methylene chloride, tetrahydrofuran, or toluene.

The amide moiety of the salicylamide may be activated by methods known in the art. For example, the amide moiety may be activated by reacting the salicylamide with an activating agent, such as an acyl halide, acyl anhydride, sulfonyl halide, or sulfonyl anhydride. The resulting salicylamide has an activating group attached to the nitrogen atom of the amide moiety. Suitable acyl halides include, but are not limited to, those described above for protecting the hydroxy moiety of the salicylamide. Preferably, the activating agent is reacted with the salicylamide in the presence of a base, such as potassium carbonate, triethylamine, or pyridine.

In the preparation of carsalam and the aforementioned derivatives thereof, the protecting and activating steps are typically performed simultaneously and the protecting and activating groups are a single group attached to both the hydroxy and amide moieties. One method of preparing carsalam and the derivatives thereof is by reacting the corresponding (unprotected and unactivated) salicylamide with an alkyl chloroformate, such as ethyl chloroformate; a phenyl chloroformate; or an imidazole alkoxy carbonyl.

Alkylation

The protected/activated salicylamide is alkylated with a dicarboxylate alkylating agent to form the dicarboxylated salicylamide. Suitable dicarboxylate alkylating agents include, but are not limited to, those having the formula

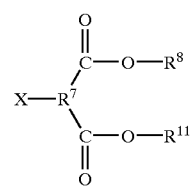

where
$R^7$ is a linear or branched, $C_1$–$C_{20}$ alkylene, alkenylene, or alkynylene;
$R^7$ is optionally substituted with $C_1$–$C_4$ alkyl, $C_1$–$C_4$ alkenyl, oxygen, nitrogen, sulfur, halogen, —OH, $C_1$–$C_4$ alkoxy, aryl, heteroaryl, or vinyl;
$R^7$ is optionally interrupted with aryl, heteroaryl, vinyl, oxygen, nitrogen, or sulfur;
$R^8$ and $R^{11}$ are independently $C_1$–$C_4$ alkyl or $C_1$–$C_4$ haloalkyl; and
X is a suitable leaving group.
Suitable leaving groups include, but are not limited to, halogens and alcohols. Two preferred leaving groups are chlorine and bromine. Preferably, $R^8$ and $R^{11}$ are independently $C_1$–$C_4$ alkyl. Preferably, $R^8$ and $R^{11}$ are the same. $R^7$ is preferably $C_4$–$C_{12}$ alkylene and more preferably $C_7$–$C_9$ alkylene.

A preferred dicarboxylate alkylating agent has the formula

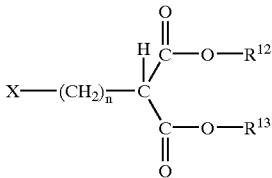

where
$R^{12}$ and $R^{13}$ are independently $C_1$–$C_4$ alkyl;
X is a suitable leaving group; and
n is an integer from 2 to 12.
Preferably, n ranges from 3 to 10, more preferably from 4 to 8, and most preferably from 6 to 8. Non-limiting examples of dicarboxylate alkylating agents include 2-(6-bromohexyl) malonic acid diethyl ester and 2-(8-bromooctyl)malonic acid diethyl ester, which are available from Allied Signal, Inc. of Morristown, N.J.

In a more preferred embodiment, $R^1$, $R^2$, $R^3$, and $R^4$ of the protected/activated salicylamide are hydrogen and n of the dicarboxylate alkylating agent is 6 or 8. According to another preferred embodiment, $R^1$, $R^2$, and $R^4$ of the protected/activated salicylamide are hydrogen, $R^3$ is chlorine, and n of the dicarboxylate alkylating agent is 2 or 6. According to yet another preferred embodiment, $R^1$, $R^3$, and $R^4$ of the protected/activated salicylamide are hydrogen, $R^2$ is methoxy, and n of the dicarboxylate alkylating agent is 6.

Many of the alkylating agents disclosed in the prior art, such as ethyl 10-bromo-decanoate and ethyl 8-bromo-octanoate as disclosed in International Publication No. WO 00/46182, are prepared from the dicarboxylate alkylating agents of the present invention. The process for converting the dicarboxylate compounds to the alkylating agents of the prior art is often expensive and time consuming. For example, ethyl 8-bromo-octanoate is prepared from 2-(6-bromohexyl)malonic acid diethyl ester by a multi-step process which includes an expensive distillation step. The process of the present invention reduces the number of synthetic steps required to prepare alkylated salicylamides and, therefore, reduces their manufacturing cost and time.

The reaction between the dicarboxylate alkylating agent and the protected/activated salicylamide is preferably carried out in the presence of a slight molar excess of protected/activated salicylamide relative to dicarboxylate alkylating agent. Generally, the molar ratio of protected/activated salicylamide to dicarboxylate alkylating agent ranges from about 1:1 to about 1:0.5, preferably from about 1:0.99 to about 1:0.8, and most preferably about 1:0.95.

The alkylating reaction is preferably performed in the presence of a suitable base, such as pyridine, picoline, tetramethylguanidine, triethylamine, diisopropylethylamine, sodium or potassium bicarbonate, sodium or potassium carbonate, or any combination of any of the foregoing. According to a preferred embodiment, the base is sodium carbonate. Generally, the reaction is performed in the presence of a slight molar excess of base relative to the protected/activated salicylamide.

The reaction may be carried out in solvents including, but not limited to, dimethylacetamide (DMAC); dimethylformamide (DMF); ketones, such as acetone, methylethylketone, and methylisobutylketone; and any combination of any of the foregoing. Preferably, the solvent is non-aqueous.

The alkylating reaction is generally performed at a temperature of from about 40 to about 80° C. The reaction is preferably performed at a temperature of from about 60 to about 80° C. and most preferably at about 70° C. The reaction is typically performed at atmospheric pressure to fall vacuum and preferably from about 22 to about 24" Hg of vacuum.

The reaction mixture prior and during the reaction preferably contains less than 5%, more preferably less than 3%, and most preferably less than 1% by weight of water, based upon 100% total weight of reaction mixture.

The reaction is generally performed for a time sufficient to ensure the complete reaction of the alkylating agent. The reaction duration may vary depending on the starting materials. Generally, the reaction is allowed to run for a time sufficient so that at least about 90% and preferably at least about 99% of the limiting reagent, i.e., the dicarboxylate alkylating agent, has been consumed, but is stopped before significant side reaction product build up. This reduces or eliminates the need for purification of the final product. Preferably, the reaction is performed for from about 2 to about 18 hours, more preferably from about 3 to about 5 hours, and most preferably about 4 hours.

Carsalam and carsalam derivatives are preferably alkylated in the presence of a slight molar excess of base. A preferred base for such an alkylation reaction is sodium carbonate. A molar excess of sodium carbonate relative to carsalam or carsalam derivative is generally used. More preferably, the carsalam or the carsalam derivative is alkylated by sequentially adding sodium carbonate to a solvent, such as those described above (e.g. DMAC); adding carsalam or the carsalam derivative to the solution; and adding a dicarboxylate alkylating agent to the solution. The alkylating agent is preferably added to the solution immediately following the addition of carsalam or carsalam derivative and more preferably within about 10 seconds after the completion of the carsalam or carsalam derivative addition. When the base, in this case sodium carbonate, is reacted with the carsalam or carsalam derivative, carsalam-sodium or carsalam derivative-sodium and sodium bicarbonate are formed. While carsalam has a solubility of about 30% in DMAC, carsalam-sodium only has a solubility of about 6% in DMAC. Sodium bicarbonate can react with the carsalam or carsalam derivative resulting in the formation of carbonic acid, which may further react to form water. Generally, water significantly reduces the efficacy of the alkylating agent. In order to minimize the reaction of sodium bicarbonate with the carsalam or carsalam derivative, the carsalam or carsalam derivative is preferably reacted with a molar excess of sodium carbonate. The water content of the reaction mixture may also be reduced by performing the reaction in a low pressure atmosphere (e.g. a vacuum).

According to another embodiment, the carsalam-sodium or carsalam derivative-sodium is isolated prior to being reacted with the alkylating agent in order to reduce water content.

The dicarboxylate salicylamide intermediate has the formula

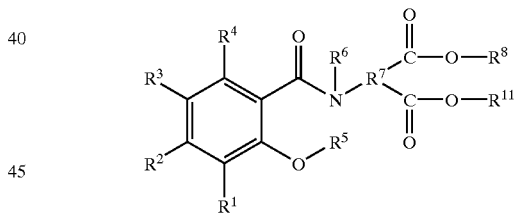

where $R^1$, $R^2$, $R^3$, $R^5$, $R^6$, $R^7$, $R^8$ and $R^{11}$ are defined as above. Non-limiting examples of dicarboxylate salicylamide intermediates of the present invention are

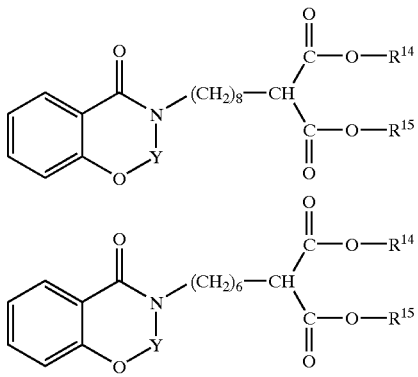

-continued

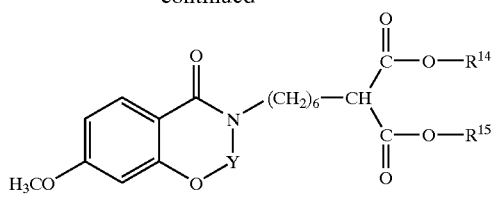

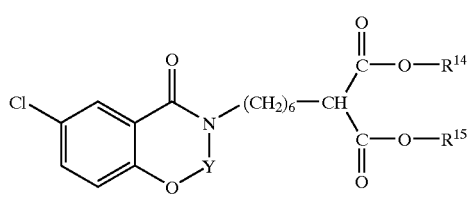

where Y is —C(O)— or

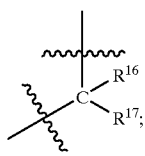

$R^{14}$ and $R^{15}$ are independently $C_1$–$C_4$ alkyl; and
$R^{16}$ and $R^{17}$ are independently hydrogen, $C_1$–$C_4$ alkyl, $C_2$–$C_4$ alkenyl, or $C_2$–$C_4$ alkynyl.

According to one embodiment, Y is —$CH_2$—. According to another embodiment, Y is —C(O)—. $R^{14}$ and $R^{15}$ are preferably methyl or ethyl.

The dicarboxylate salicylamide intermediate is then (a) deprotected and deactivatied, (b) optionally, hydrolyzed, and (c) optionally, decarboxylated to yield the alkylated salicylamide. Steps (a) and (b) may be performed before or after step (c). Preferably, step (c) is performed after steps (a) and (b). Typically, this process entails the removal of the protecting and activating groups and, optionally, one of the carboxylate moieties. Optionally, the carboxylate moiety or moieties of the alkylated salicylamide may be hydrolyzed to form a carboxylic acid moiety or carboxylic acid moieties or carboxylate salt. The protecting and activating groups and one of the carboxylate groups may be removed and the remaining carboxylate group may be hydrolyzed by acidic, basic and/or neutral hydrolysis as known in the art. Neutral hydrolysis may be performed, for example, with superheated water at a temperature of from about 100 to about 250° C.

Deprotection

The salicylamide may be deprotected by any method known in the art, such as acidic, basic, or neutral hydrolysis. Deprotection is preferably performed by basic hydrolysis. Basic hydrolysis may be performed, for example, with aqueous sodium carbonate or aqueous sodium hydroxide. According to one embodiment, basic hydrolysis is performed with aqueous sodium hydroxide at a temperature of from about 78 to about 98° C.

Another method of deprotecting is by acidic hydrolysis. Acidic hydrolysis may be performed, for example, with aqueous hydrochloric acid or aqueous trifluoroacetic acid. For example, acidic hydrolysis may be performed with aqueous hydrochloric acid in acetone at a temperature of from about 25 to about 65° C. According to one embodiment, acidic hydrolysis is performed at a pH of about 3.5 to 4.5 and preferably at about 4. The acidic hydrolysis process may also deactivate the salicylamide.

Deactivation

The activating group may be removed by any method known in the art. When acidic or basic hydrolysis is performed to deprotect the salicylamide, the activating group may be removed by neutralization. For example, when deprotection is performed by basic hydrolysis, the salicylamide may be deactivated by adding an aqueous acid, such as hydrochloric acid or aqueous trifluoroacetic acid. When deprotection is performed by acidic hydrolysis, the salicylamide may be deactivated by adding an aqueous basic.

Hydrolysis

Optionally, the alkylated salicylamide may be further reacted to modify the end group of the allcylating moiety, i.e., $R^8$ or $R^{11}$, as well as the oxygen group attached to the phenyl ring. For example, the end group —CN or —C(O)O—$CH_2$—$CH_3$ may be modified to —COOH or a salt thereof. This may be accomplished by methods known in the art, such as neutralization and acidic, basic, and neutral hydrolysis. Generally, hydrolysis of the salicylamide is performed by neutralizing the deprotected and deactivated salicylamide. When the salicylamide is deprotected by basic hydrolysis, the free acid of the salicylamide is, for example, recovered by neutralization with an aqueous acid, such as hydrochloric acid.

Decarboxylation

If a monocarboxylic salicylamide is desired, the prepared alkylated salicylamide may be decarboxylated. The decarboxylation step is performed either before or after the deprotecting and deactivating steps and optional hydrolysis step. Preferably, decarboxylation is performed after the deprotecting and deactivating steps and optional hydrolysis step.

The decarboxylation step removes one of the carboxylate moieties from the alkylated salicylamide (i.e. one of the two carboxyl groups at the end of the chain $R^7$). Decarboxylation can be performed by any method known in the art, such as acidic hydrolysis as discussed above. In order to control foaming due to the release of carbon dioxide, the reaction may be performed in the presence of acetone.

Decarboxylation can also be performed by heating the alkylated salicylamide in a high boiling point organic solvent, such as xylenes, toluene, heptane, dimethyl acetamide (DMA or DMAC), dimethyl formamide (DMF), methyl sulfoxide, isoparaffins (e.g. isopar-G, isopar-H, isopar-L, and isopar-K available from Exxon Chemicals of Houston, Tex.), and any combination of any of the foregoing. The organic solvent preferably has a boiling point of at least 110° C. and more preferably of at least 140° C. The decarboxylation reaction is preferably performed at a temperature ranging from about 140 to about 200° C. and more preferably ranging from about 140 to about 160° C. The temperature at which the reaction is performed should be sufficient to remove one of the carboxylate groups at the end of the chain $R^7$.

Preferably, any water in the reaction mixture is removed prior to heating. Water may be removed from a reaction mixture containing the free acid of the alkylated salicylamide (which is formed if the alkylated salicylamide is hydrolyzed as described in the "Hydrolysis" section above) as follows. The alkylated salicylamide is mixed with an organic solvent in which it is soluble, such as xylenes. The aqueous layer is then extracted, which in this case is the lower layer, leaving the alkylated salicylamide in xylenes. The reaction mixture may then be heated to decarboxylate the alkylated salicylamide.

The reaction mixture prior and during the decarboxylation reaction preferably contains less than 5%, more preferably less than 3%, and most preferably less than 1% by weight of water, based upon 100% total weight of reaction mixture.

The decarboxylation step may also be performed neat (i.e. without a solvent) by heating the deprotected, deactivated, and, optionally, hydrolyzed alkylated salicylamide to a temperature ranging from about 140 to about 200° C.

The deprotecting, deactivating, hydrolyzing, and decarboxylating steps may be performed at a temperature of from about 20 to about 200° C.

Suitable solvents for the protected/activated alkylated salicylamide in the deprotecting, deactivating, decarboxylating, and hydrolyzing step include, but are not limited to, organic solvents, such as ethanol, dimethylacetamide (DMAC), dimethylformamide (DMF), ketones (e.g. acetone, methylethylketone, and methylisobutylketone), and any combination of any of the foregoing.

When the protected/activated salicylamide is carsalam or a derivative thereof, the alkylated salicylamide may be deprotected by hydrolysis, such as basic hydrolysis. This causes the bonds between the carbonyl group and the adjacent oxygen atoms to cleave, thereby deprotecting the hydroxyl moiety. Hydrolysis may be carried out under conditions known in the art.

After hydrolysis of the carsalam or carsalam derivative, the activated salicylamide may be deactivated by methods known in the art. For example, hydrochloric acid may be added to the activated alkylated salicylamide until the pH of the reaction mixture is from about 3.5 to about 4.5 or until the pH is less than about 4. This causes the bond between the carbonyl moiety and the nitrogen atom of the amide moiety of the salicylamide to cleave and release carbon dioxide. The hydrochloric acid may also remove one of the carboxylate moieties and hydrolyze the remaining carboxylate moiety.

Alternatively, after hydrochloric acid is added to deactivate the alkylated salicylamide, the alkcylated salicylamide can be decarboxylated by heating it in xylenes or other high boiling point organic solvent, such as those discussed above, to reflux or near reflux. For example, when xylene is used as the solvent, the mixture is preferably heated to a temperature ranging from about 105 to about 140° C.

Salts of the alkylated salicylamide may be formed by any method known in the art. For example, the acid form of the alkylated salicylamide, i.e., where the alkylated salicylamide has a —COOH moiety, may be converted into the corresponding sodium salt by reacting it with sodium hydroxide. Suitable salts include, but are not limited to, organic and inorganic salts, for example alkali-metal salts, such as sodium, potassium and lithium; alkaline-earth metal salts, such as magnesium, calcium or barium; amnmonium salts; basic amino acids, such as lysine or arginine; and organic amines, such as dimethylamine or pyridine. Sodium salts include, but are not limited to, mono-, di-, and other multi-valent sodium salts. A preferred salt is the disodium salt. The salts may also be solvates, including ethanol solvates, and hydrates. The term "solvate" as used herein includes, but is not limited to, a molecular or ionic complex of molecules or ions of a solvent, such as ethanol, with ions or molecules of the compounds of the present invention.

The present method may be used to prepare alkylated salicylamides having the formula

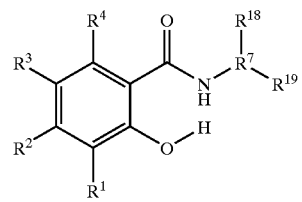

where
$R^1$, $R^2$, $R^3$, $R^4$, and $R^7$ are defined as above; and
$R^{18}$ and $R^{19}$ are independently hydrogen, carboxyl or a salt thereof, carboxylate, nitrile, halogen, ester, amine or salt thereof, alcohol, or thiol and at least one of $R^{18}$ and $R^{19}$ is not hydrogen. According to a preferred embodiment, $R^{19}$ is hydrogen. Non-limiting examples of such compounds include N-(8-[2-hydroxybenzoyl]-amino)caprylic acid, N-(9-[2-hydroxybenzoyl]-amino)nonanoic acid, N-(10-[2-hydroxybenzoyl]amino)decanoic acid, N-(5-chlorosalicyloyl)-8-aminocaprylic acid, N-(4-methoxysalicyloyl)-8-aminocaprylic acid, and salts, solvates, and hydrates thereof.

The alkylated salicylamides of the present invention may be purified by recrystallization or fractionation on one or more chromatographic supports. Fractionation may be performed on suitable chromatographic supports, such as silica gel or alumina, using solvent mixtures such as acetic acid/butanol/water as the mobile phase; reverse phase column supports using trifluoroacetic acid/acetonitrile mixtures as the mobile phase; and ion exchange chromatography using water as the mobile phase. The alkylated salicylamides may also be purified to remove impurities, such as inorganic salts, by extraction with a lower alcohol, such as methanol, butanol, or isopropanol.

The method of the present invention uses readily available and inexpensive starting materials and provides a cost-effective method for preparing and isolating alkylated salicylamides. The method is simple to perform and is amenable to industrial scale-up for commercial production.

Active Agent Delivery Systems
Dicarboxylate Delivery Agent Compounds

The dicarboxylate delivery agent compounds of the present invention include the free acids of the dicarboxylated salicylamide intermediates of the present invention (i.e. when $R^8$ and $R^{11}$ are hydrogen) and salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts, di-sodium salts, and trisodium salts. The salts may also be solvates, including ethanol solvates, and hydrates.

The delivery agent compounds may be in the form of the free amine or salts thereof. Suitable salts include, but are not limited to, organic and inorganic salts, for example hydrochloride salts, acetate or citrate.

Salts of the delivery agent compounds of the present invention may be prepared by methods known in the art. For example, sodium salts may be prepared by dissolving the delivery agent compound in ethanol and adding aqueous sodium hydroxide. In addition, poly amino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids. One or more of the amino acids or peptide units may be acylated or sulfonated.

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of mucopolysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including $\alpha$, $\beta$ and $\gamma$; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof. A preferred active agent is calcitonin and more preferably salmon calcitonin.

The composition of the present invention comprises one or more delivery agent compounds of the present invention, and one or more active agents. In one embodiment, one or more of the delivery agent compounds, or salts of these compounds, or poly amino acids or peptides of which these compounds or salts form one or more of the units thereof, may be used as a delivery agent by mixing with the active agent prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, and any combination thereof.

The delivery agent compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the delivery agent compounds and active agents have utility in the delivery of active agents to biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery), or in delivering the active agent at a specific time, or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference (54$^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
| --- | --- |
| Growth hormones | Growth disorders |
| Interferons, including α, β, and γ. | Viral infection, including chronic cancer and multiple sclerosis |
| Interleukin-1; interleukin-2. | Viral infection; cancer |
| Insulin; Insulin-like growth factor IGF-1. | Diabetes |
| Heparin | Thrombosis; prevention of blood coagulation |
| Calcitonin. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |

-continued

| Active Agent | Disease and Physiological Effect |
| --- | --- |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium; Vancomycin | Asthma; allergies |
| Desferrioxamine (DFO) | Iron overload |
| Parathyroid hormone (PTH), including its fragments. | Osteoporosis; Diseases of the bone |
| Antimicrobials | Infection including gram-positive bacterial infection |
| Vitamins | Vitamin deficiencies |
| Bisphosphonates | Osteoporosis; Paget's disease; Inhibits osteoclasts |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent is readily assessed by measuring a known pharmacological activity in blood, e.g., an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The invention will now be illustrated in the following non-limiting examples which are illustrative of the invention but are not intended to limit the scope of the invention. All percentages are by weight unless otherwise indicated.

EXAMPLE 1

Preparation of N-(2-hydroxybenzoyl)-10-amino)-decanoic acid 20 g (0.123 mole) carsalam (available from Sigma-Aldrich of Shiboygan Falls, Wis.), 43.16 g (0.123 mole) 2-(8-bromooctyl)malonic acid diethyl ester (available from Allied Signal, Inc. of Morristown, N.J.), 15.52 g (0.137 mole) sodium carbonate (available from Sigma-Aldrich of St. Louis, Mo.) and 100 mL dimethylacetamide (DMA) (available from Sigma-Aldrich) were heated to about 75° C. for about 5 hours. The solids were filtered off and the filtrate was stirred in 2N sodium hydroxide at 45° C. for a total of about 9 hours to form N-(2-hydroxybenzoyl)-10-amino)-decanoic acid. Formation of the decanoic acid was evident. It was then heated to about 100° C. to determine if the decanoic acid was indeed forming. HPLC of the reaction showed the 9.09 peak transforms to 8.79, 7.23, 5.78 min. Last HPLC showed 49.6 area % of peak 5.78 min, indicating formation of about 50% (w/w) of the decanoic acid.

In a separate reaction, the same reagents described above were heated to about 100° C. for about 2 hours. The solids were filtered off and washed with ethanol. Water was added to the filtrate and the DMA was removed in vacuo. The aqueous layer was extracted with ethyl acetate (3×150 mL), combined and concentrated in vacuo. The resulting oil was stirred in 2N sodium hydroxide at 45° C. for about 4 hours.

HPLC was performed by dissolving approximately 1 mg of the product per mL of 50% aqueous acetonitrile solution.

The injection size was 20 mL The HPLC parameters were as follows:

| | |
|---|---|
| Column: Higgins Kromasil 100 C18 | Particle Size: 5 μm |
| Column Length: 5 cm | Column Diameter: 4.6 mm |
| Mobile Phase A: water, acetonitrile, acetic acid (950:50:1) | |
| Mobile Phase B: water, acetonitrile, acetic acid (50:950:1) | |
| Gradient: 0 to 100% mobile phase B, 10 minutes | Flow Rate: 3 mL per minute |
| Back Pressure: 1100 psi | Column Temperature: ambient |
| Detector: UV 220 nm | |

HPLC of the reaction showed the 8.9 peak transforms to 8.6, 7.0, 5.7 min. Final HPLC showed 35% area % of 5.7 peak.

EXAMPLE 2

Preparation of N-(8-[2-hydroxybenzoyl]amino) caprylic acid

N-(8-[2-hydroxybenzoyl]amino)caprylic acid was prepared by the procedure described in Example 1 with the appropriate starting materials.

A flow chart of this procedure is shown below.

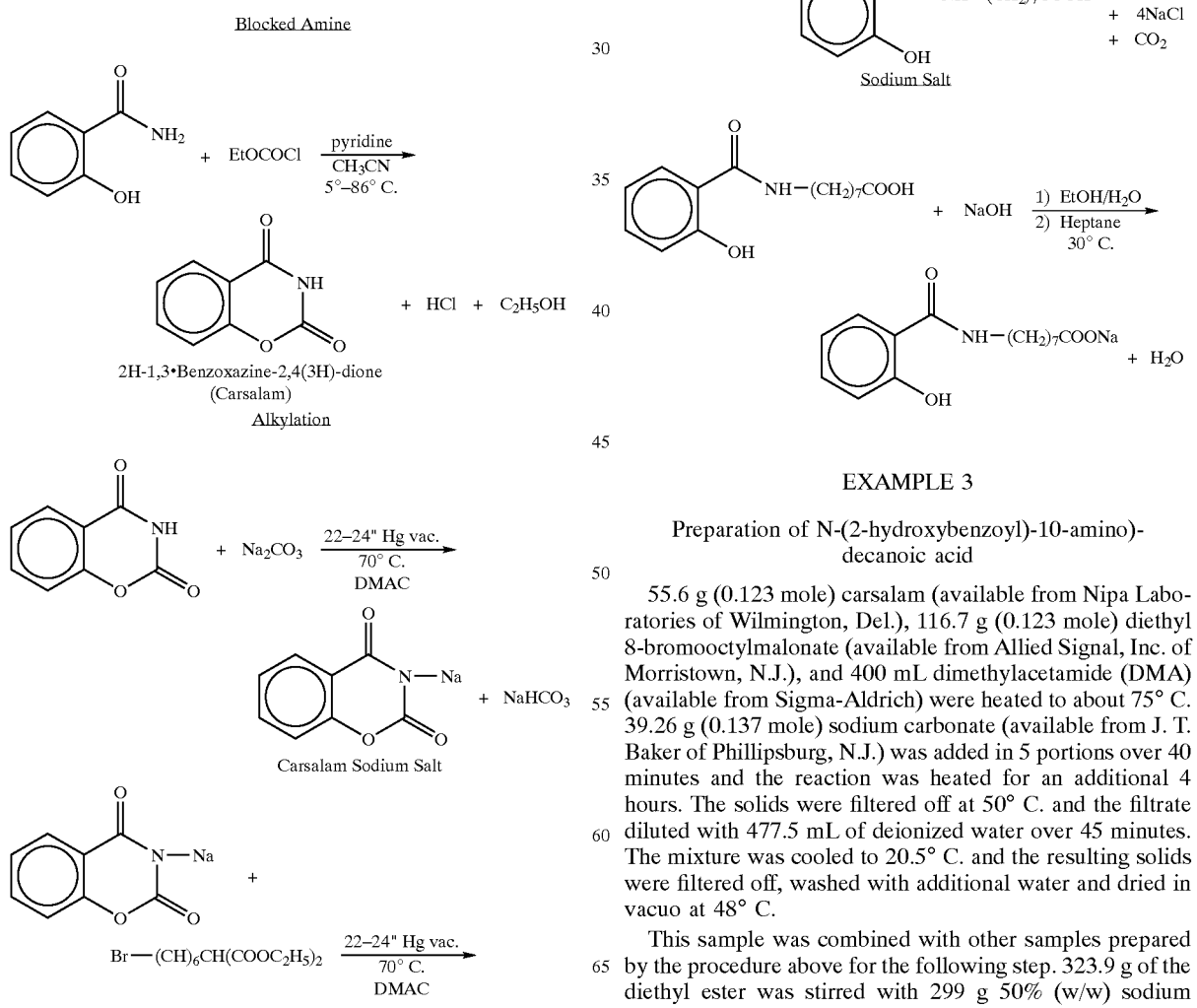

EXAMPLE 3

Preparation of N-(2-hydroxybenzoyl)-10-amino)-decanoic acid 55.6 g (0.123 mole) carsalam (available from Nipa Laboratories of Wilmington, Del.), 116.7 g (0.123 mole) diethyl 8-bromooctylmalonate (available from Allied Signal, Inc. of Morristown, N.J.), and 400 mL dimethylacetamide (DMA) (available from Sigma-Aldrich) were heated to about 75° C. 39.26 g (0.137 mole) sodium carbonate (available from J. T. Baker of Phillipsburg, N.J.) was added in 5 portions over 40 minutes and the reaction was heated for an additional 4 hours. The solids were filtered off at 50° C. and the filtrate diluted with 477.5 mL of deionized water over 45 minutes. The mixture was cooled to 20.5° C. and the resulting solids were filtered off, washed with additional water and dried in vacuo at 48° C.

This sample was combined with other samples prepared by the procedure above for the following step. 323.9 g of the diethyl ester was stirred with 299 g 50% (w/w) sodium hydroxide (available from J. T. Baker) and 650 mL of deionized water. The mixture was heated to 82.5° C. over 9 hours and monitored by HPLC. This hydrolysis solution was slowly added to a mixture of 368.9 g concentrated hydrochloric acid (available form J. T. Baker) and 1L deionized water. The mixture was cooled to 25° C. and the resulting solids were filtered off and air-dried.

90.0 g of the diacid produced above and 500 mL xylenes (available from Sigma-Aldrich) were heated to reflux for 18 hours. Any residual water was removed by distillation before reflux was reached. At 107.5° C., gas evolution was evident. The reaction was monitored by the collection of carbon dioxide in a sodium hydroxide trap. The solution was cooled to room temperature and the resulting crystals were collected by filtration. The structure of the final compound was confined by $^1$H NMR.

Analytical:

A sample for HPLC analysis was prepared by dissolving approximately 1 mg of the sample per mL of 60% (w/w) aqueous acetonitrile. The injection size was 20 µL. A retention time of 20.75 minutes was observed under the following conditions.

| | |
|---|---|
| Column: Higgins CLIPEUS Phenyl | Particle Size: 5 µm |
| Column Length: 15 cm | Column Diameter: 4.6 mm |
| Mobile Phase A: methanol, water, acetic acid (350:650:5) | |
| Mobile Phase B: methanol, water, acetic acid (950:50:5) | |
| Flow Rate: 0.7 mL per minute | Column Temperature: ambient |
| Detector: UV 244 nm | |

Program: The HPLC program began with 100% mobile phase A for a wash out period of 8 minutes then the sample was injected. At the same time the sample was injected, a linear gradient began which changed to 100% mobile phase B over a 30 minute period. 100% mobile phase B was maintained for 5 minutes, then a linear gradient was used to go back to 100% mobile phase A in 2 minutes. The 8 minute wash out cycle was repeated before the next sample was injected.

$^1$H NMR Analysis: (d$_6$-DMSO), 300 mHz: δ 12.40, s, 1H (COOH); δ 8.8, t, 1H (NH); δ 7.85, dd, 1H (H ortho to hydroxy); δ 7.4, dt, 1H, (H para to amide); δ 6.9, t, 1H, (H para to hydroxy); δ 3.25, q, 2H (CH$_2$ adjacent to NH); δ 2.20, t, 2H (CH$_2$ adjacent to COOH); δ 1.51, m, 4H (aliphatic CH$_2$ beta to NH and CH$_2$ beta to COOH); δ 1.29, m, 10H (remaining aliphatic CH$_2$).

A flow chart of this procedure is shown below.

Blocked Amine

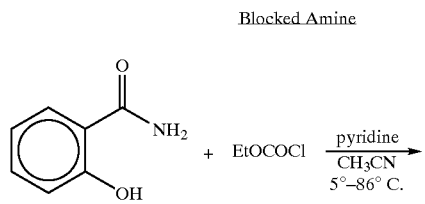

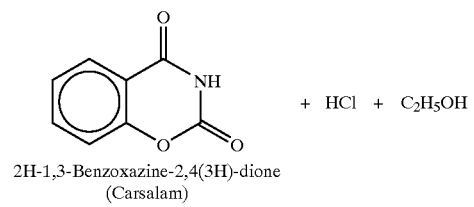

2H-1,3-Benzoxazine-2,4(3H)-dione
(Carsalam)

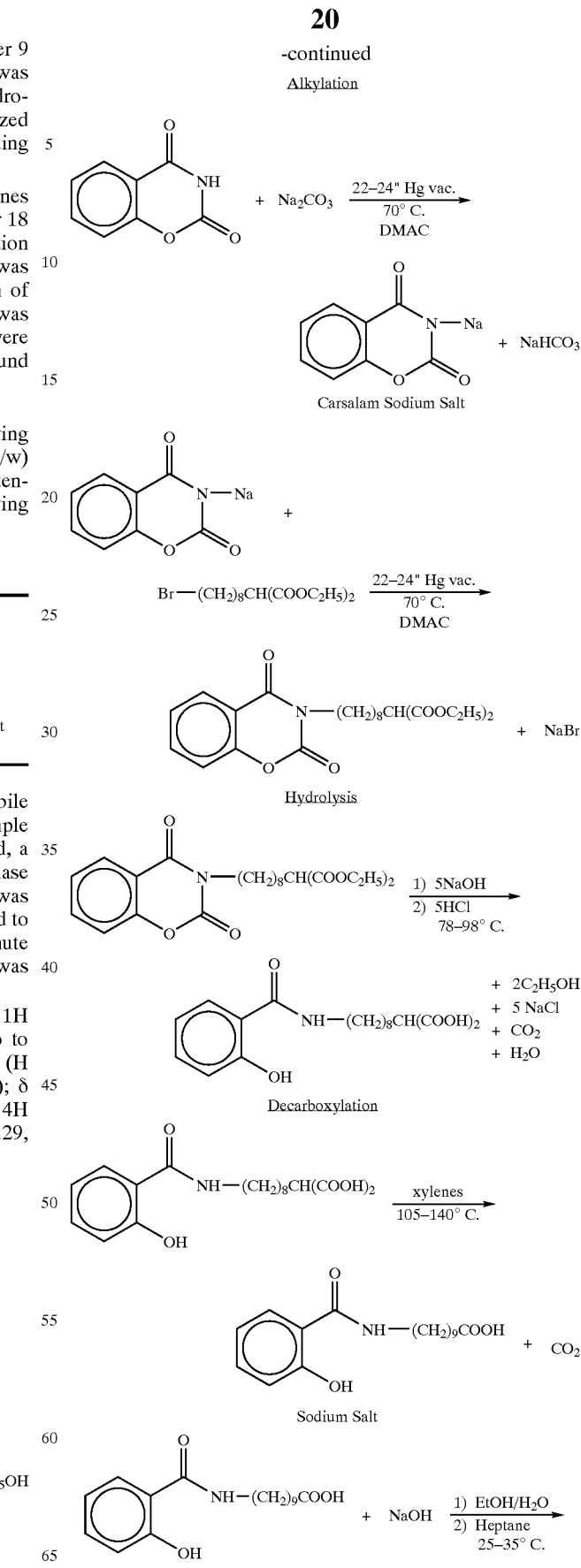

-continued

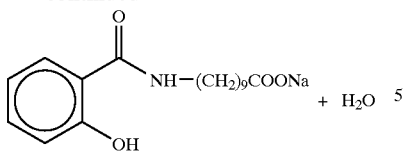

+ H₂O

All patents, patent applications, literature publications, and test methods cited herein are hereby incorporated by reference.

Many variations of the present invention will suggest themselves to those skilled in the art in light of the above detailed disclosure. All such modifications are within the full intended scope of the appended claims.

What is claimed is:

1. A method of preparing a protected dicarboxylated salicylamide from a protected and activated salicylamide that is protected to prevent reaction of the hydroxy moiety and activated at the Nitrogen atom of the amide group, the method comprising the step of (a) alkylating the protected and activated salicylamide at the Nitrogen atom of the amide group with a dicarboxylate alkylating agent to form the protected dicarboxylated salicylamide.

2. A method of preparing an alkylated salicylamide from a protected and activated salicylamide that is protected to prevent reaction of the hydroxy moiety and activated at the Nitrogen atom of the amide group, the method comprising the steps of (a) alkylating the protected and activated salicylamide at the Nitrogen atom of the amide group with a dicarboxylate alkylating agent to form a protected and activated dicarboxylated salicylamide, and (b)(i) deprotecting, (ii) deactivating, and (iii) decarboxylating the protected and activated dicarboxylated salicylamide to form the alkylated salicylamide.

3. The method of claim 2, wherein the protected and activated salicylamide has the formula

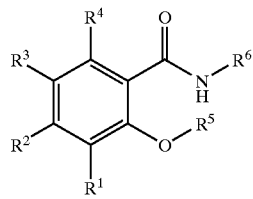

wherein
R¹, R², R³, and R⁴ are independently hydrogen; halogen; $C_1$–$C_4$ alkoxy, optionally substituted with —OH or F; —OH; $C_1$–$C_4$ alkyl, optionally substituted with —OH or F; —COOH; —OC(O)CH₃; —SO₃H; nitrile; or —NR⁹R¹⁰;
R⁹ and R¹⁰ are independently hydrogen, $C_1$–$C_4$ alkyl, or oxygen;
R⁵ is a protecting group;
R⁶ is an activating group; or
R⁵ and R⁶ are combined to form a substituted or unsubstituted cyclic group.

4. The method of claim 3, wherein the protected and activated salicylamide has the formula

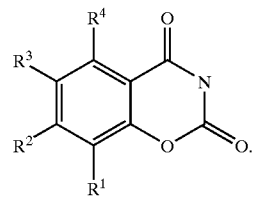

5. The method of claim 2, wherein the dicarboxylate alkylating agent has the formula

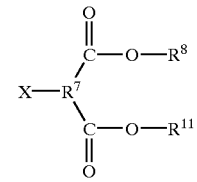

wherein
R⁷ is a linear or branched, $C_1$–$C_{20}$ alkylene, alkenylene, or alkynylene;
R⁷ is optionally substituted with $C_1$–$C_4$ alkyl, $C_1$–$C_4$ alkenyl, oxygen, nitrogen, sulfur, halogen, —OH, $C_1$–$C_4$ alkoxy, aryl, heteraryl, or vinyl;
R⁷ is optionally interrupted with aryl, heteroaryl, vinyl, oxygen, nitrogen, or sulfur;
R⁸ and R¹¹ are independently $C_1$–$C_4$ alkyl or $C_1$–$C_4$ haloalkyl; and
X is a suitable leaving group.

6. The method of claim 2, wherein the molar ratio of protected and activated salicylamide to dicarboxylate alkylating agent is from about 1:1 to about 1:0.5.

7. The method of claim 2, wherein the alkylating step is performed in the presence of a base.

8. The method of claim 7, wherein the molar ratio of base to protected and activated salicylamide is greater than 1.

9. The method of claim 8, wherein the base is pyridine, picoline, tetramethylguanidine, triethylamine, diisopropylethylamine, sodium bicarbonate, potassium bicarbonate, sodium carbonate, potassium carbonate, or any combination of any of the foregoing.

10. The method of claim 9, wherein the base is sodium carbonate.

11. The method of claim 2, wherein the alkylating step is performed at a temperature of from about 40 to about 80° C.

12. The method of claim 11, wherein the alkylating step is performed at a temperature of from about 60 to about 80° C.

13. The method of claim 2, wherein the protected and activated dicarboxylate salicylamide has the formula

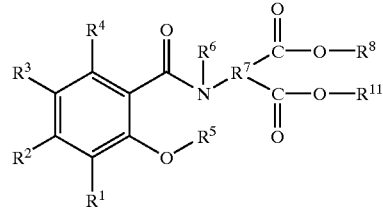

where
R¹, R², R³, and R⁴ are independently hydrogen; halogen; $C_1$–$C_4$ alkoxy, optionally substituted with —OH; or F;

—OH; $C_1$–$C_4$ alkyl, optionally substituted with —OH or F; —COOH; —OC(O)CH$_3$; —SO$_3$H; nitrile; or —NR$^9$R$^{10}$;

$R^9$ and $R^{10}$ are independently hydrogen, $C_1$–$C_4$ alkyl, or oxygen;

$R^5$ is a protecting group;

$R^6$ is an activating group; or $R^5$ and $R^6$ are combined to form a substituted or unsubstituted cyclic group;

$R^7$ is a linear or branched, $C_1$–$C_{20}$ alkylene, alkenylene, or alkynylene;

$R^7$ is optionally substituted with $C_1$–$C_4$ alkyl, $C_1$–$C_4$ alkenyl, oxygen, nitrogen, sulfur, halogen, —OH, $C_1$–$C_4$ alkoxy, aryl, heteraryl, or vinyl;

$R^7$ is optionally interrupted with aryl, heteroaryl, vinyl, oxygen, nitrogen or sulfur;

$R^8$ and $R^{11}$ are independently $C_1$–$C_4$ alkyl or $C_1$–$C_4$ haloalkyl; and $R^9$ and $R^{10}$ are independently hydrogen, $C_1$–$C_4$ alkyl, or oxygen.

14. The method of claim 2, wherein deprotecting and deactivating the protected and activated dicarboxylated salicylamide comprises performing basic hydrolysis and acidic hydrolysis on the protected and activated dicarboxylated salicylamide.

15. The method of claim 2, wherein the deprotecting, deactivating, and decarboxylating step comprises performing basic hydrolysis and acidic hydrolysis on the protected and activated dicarboxylated salicylamide.

16. The method of claim 2, wherein the deprotecting step comprises hydrolysis.

17. The method of claim 16, wherein the deprotecting step comprises basic hydrolysis.

18. The method of claim 17, wherein the deactivating step comprises neutralization.

19. The method of claim 2, further comprising hydrolyzing one or more carboxyl moieties of the alkylated salicylamide after steps (b)(i) an (b)(ii) to form the free acid of the dicarboxylated salicylamide.

20. The method of claim 19, wherein the decarboxylating step is performed after the deprotecting, deactivating, and hydrolyzing steps.

21. The method of claim 2, wherein decarboxylating comprises heating the dicarboxylated salicylamide in an organic solvent to a temperature ranging from about 140 to about 200° C.

22. The method of claim 21, wherein the organic solvent has a boiling point of at least about 110° C.

23. The method of claim 21, wherein the organic solvent is selected from xylenes, toluene, heptane, dimethyl acetamide, dimethyl formamide, methyl sulfoxide, isoparaffins, and any combination of any of the foregoing.

24. The method of claim 2, wherein the alkylated salicylamide has the formula

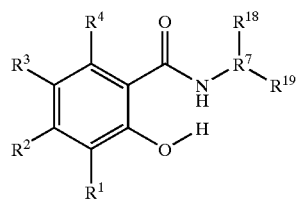

wherein $R^1$, $R^2$, $R^3$, and $R^4$ are independently hydrogen; halogen; $C_1$–$C_4$ alkoxy, optionally substituted with —OH or F; —OH; $C_1$–$C_4$ alkyl, optionally substituted with —OH or F; —COOH; —OC(O)CH$_3$; —SO$_3$H; nitrile; or —NR$^9$R$^{10}$;

$R^7$ is a linear or branched, $C_1$–$C_{20}$ alkylene, alkenylene, or alkynylene;

$R^7$ is optionally substituted with $C_1$–$C_4$ alkyl, $C_1$–$C_4$ alkenyl, oxygen, nitrogen, sulfur, halogen, —OH, $C_1$–$C_4$ alkoxy, aryl, heteraryl, or vinyl;

$R^7$ is optionally interrupted with aryl, heteroaryl, vinyl, oxygen, nitrogen, or sulfur;

$R^9$ and $R^{10}$ are independently hydrogen, $C_1$–$C_4$ alkyl, or oxygen; and $R^{18}$ and $R^{19}$ are independently hydrogen, carboxyl or a salt thereof, carboxylate, nitrile, halogen, ester, amine or salt thereof, alcohol, or thiol and at least one of $R^{18}$ and $R^{19}$ is not hydrogen, and $R^{18}$ and $R^{19}$ are not both selected from carboxyl or a salt thereof, or carboxylate.

25. The method of claim 24, wherein $R^{19}$ is hydrogen.

26. The method of claim 2, wherein the alkylated salicylamide is N-(2-hydroxybenzoyl)-7-amino)heptanoic acid or a salt thereof.

27. The method of claim 2, wherein the alkylated salicylamide is N-(2-hydroxybenzoyl)-8-amino)octanoic acid or a salt thereof.

28. The method of claim 2, wherein the alkylated salicylamide is N-(2-hydroxybenzoyl)-10-amino)decanoic acid or a salt thereof.

29. The method of claim 2, wherein the alkylated salicylamide is N-(2-hydroxy-5-chlorobenzoyl)-4-amino)butyric acid or a salt thereof.

30. The method of claim 2, wherein the alkylated salicylamide is N-(2-hydroxy-5-chlorobenzoyl)-8-amino)octanoic acid or a salt thereof.

31. The method of claim 2, wherein the alkylated salicylamide is N-(2-hydroxy-4-methoxybenzoyl)-8-amino) octanoic acid or a salt thereof.

32. A method of preparing an alkylated salicylamide from a protected and activated dicarboxylated salicylamide that is protected to prevent reaction of the hydroxy moiety and activated at the Nitrogen atom of the amide group comprising the step of deprotecting, deactivating, decarboxylating, and hydrolyzing the protected and activated dicarboxylated salicylamide to form the alkylated salicylamide.

* * * * *